United States Patent [19]

Mrusek et al.

[11] Patent Number: 5,098,897
[45] Date of Patent: Mar. 24, 1992

[54] SYNERGISTIC INSECTICIDAL COMPOSITIONS

[75] Inventors: Klaus Mrusek, Bergisch Gladbach; Fritz Maurer, Wuppertal, both of Fed. Rep. of Germany

[73] Assignee: Bayer Aktiengesellschaft, Leverkusen, Fed. Rep. of Germany

[21] Appl. No.: 608,056

[22] Filed: Oct. 31, 1990

[30] Foreign Application Priority Data

Dec. 6, 1989 [DE] Fed. Rep. of Germany ....... 3940267

[51] Int. Cl.⁵ .................... A01N 37/34; A01N 53/00; A01N 57/00
[52] U.S. Cl. ..................................... 514/86; 514/521; 514/531
[58] Field of Search ........................... 514/86, 521, 531

[56] References Cited

U.S. PATENT DOCUMENTS 4,183,950 1/1980 Naumann et al. .................. 560/124
4,882,321 11/1989 Maurer et al. .......................... 514/86

OTHER PUBLICATIONS

Worthing et al., The Pesticide Manual, 8 ed., pp. 205 and 206 (1987).

*Primary Examiner*—Allen J. Robinson
*Attorney, Agent, or Firm*—Sprung Horn Kramer & Woods

[57] ABSTRACT

Synergistic insecticidal compositions comprising (I) O-methyl thionoethanephosphonate of the formula

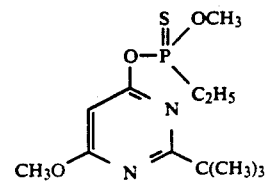

and (II) at least one member selected from the group consisting of (4-fluoro-3-phenoxy)-2-cyanobenzyl 2,2-dimethyl-3-(2', 2'-dichlorovinyl)-cyclopropanecarboxylate (cyfluthrin) and 2,3,5,6-tetrafluorobenzyl 2,2-dimethyl-3-(2', 2'-dichlorovinyl)-cyclopropanecarboxylate.

5 Claims, No Drawings

SYNERGISTIC INSECTICIDAL COMPOSITIONS

The present invention relates to new insecticidal active compound combinations of phosphonic acid esters and pyrethroids.

Phosphonic acid esters and their insecticidal activity, in particular against diptera, have been disclosed (compare DE-OS (German Published Specification) 3,704,089).

Pyrethroids and their insecticidal activity have been disclosed (compare DE-OS (German Published Specification) 2,709,264 corresponding to U.S. Pat. No. 4,218,469, DE-OS (German Published Specification) 2,658,074 corresponding to U.S. Pat. No. 4,183,950).

Mixtures of phosphoric acid esters and pyrethroids have also been described (compare DE-OS (German Published Specification) 2 757 769, DE-OS (German Published Specification) 3,017,638 and DE-OS (German Published Specification) 2,757,768). It can be inferred from these references that pyrethroids and phosphoric acid esters sometimes have a synergistic or potentiating effect.

In DE-OS (German Published Specification) 2,928,465, it is mentioned that a potentiation of the action also occurs with mixtures of pyrethorids and certain phosphonic acid esters. However, no examples of such mixtures of pyrethroids and phosphonic acid esters are given. The potentiating effect is only shown with the aid of mixtures of pyrethroids and phosphoric acid esters.

The occurrence of resistant strains of flies necessitates the use of higher and higher active compound concentrations. There is therefore interest in active compounds or active compound combinations which show a good action against resistant strains of flies at low application rates.

The following have been found:

1. New mixtures of O-(6-methoxy-2-tert.-butyl-pyrimidin-4-yl) O-methyl thionoethanephosphonate of the formula

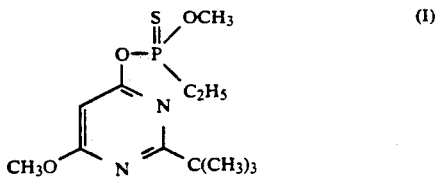

and (4-fluoro-3-phenoxy)-α-cyanobenzyl 2,2-dimethyl-3-(2',2',-dichlorovinyl)-cylcopropanecarboxyle (cyfluthrin) or 2,3,5,6-tetrafluorobenzyl 2,2-dimethyl-3-(2',2',-dichlorovinyl)-cyclopropanecarboxylate (active compound II).

2. The use of the new mixtures as in (I) for controlling insects, in particular resistant flies.

The combination of these active compounds in this case surprisingly shows a potentiation of their action which goes beyond the purely additive effect.

The active compounds are disclosed in the abovementioned literature sources.

The weight ratios of the active compounds to one another can vary within relatively wide ranges. Preferred active compound combinations are those in which one part by weight of one of the two other active compounds is present per 5-50 parts by weight of active compound of the formula I.

Particularly preferred active compound combinations are those comprising 5-25 parts by weight of active compound of the formula I and 1 part by weight of active compound II. Particularly preferred active compound combinations are those comprising 10-50 parts by weight of active compound of the formula I and 1 part by weight of cyfluthrin.

The active compound combinations are suitable for controlling arthropods, in particular insects, which are encountered in the household and hygiene field, and in the protection of stored products and of materials but also in agriculture and forestry. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni. Carpocapsa pomonella,* Pieris spp., Chilo spp., *Pyrausta nubilalis, Ephestia kuehniella, Galleria mellonella, Tineola bissel-*

*liella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

The active compound combinations according to the invention are distinguished by outstanding insecticidal activity; in particular for controlling resistant diptera, such as, for example, *Musca domestica.* Their action also persists for a very long time on basic substrates, such as, for example, on limed walls, and also PVC, clay, tiles, wood, varnished wood etc.

The active compound combinations according to the invention are very particularly preferably used in the household and hygiene field for controlling the diptera resistant to many insecticides, such as, for example, *Musca domestica.*

The active compound combinations according to the invention are also suitable for controlling arthropods, in particular insects, which occur in the keeping of agricultural productive animals, such as, for example, cattle, sheep, goats, horses, pigs, donkeys, camels, buffalo, rabbits, hens, turkeys, ducks, geese, and other household animals, such as, for example, dogs, cats and caged birds, and also so-called experimental animals, such as, for example, hamsters, guinea-pigs, rats and mice. By controlling these insects, irritations and yield reductions (in meat, milk, wool, hides, eggs, etc.) should be avoided so that more economical and simpler keeping of animals becomes possible through the use of the active compounds according to the invention.

The active compounds according to the invention are used in the animal-keeping field in a known manner by applying suitable formulations, for example by spraying, dusting or painting the environment of the animals (for example stalls) or, if appropriate, also by dermal use in the form, for example, of dipping, spraying, pouring-on and spotting-on, washing and powdering-in, and also with the aid of active compound-containing moulded articles, such as neckbands, ear tags, tail tags, limb bands, halters, marking devices, etc.

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations. The active compounds are moreover suitable for use in heat-dependent and heat-independent evaporator systems, such as offended paper, cardboard, felt, etc.

These formulations are produced in a known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.001 and 95 per cent by weight of active compounds, preferably between 0.02 and 90%.

The active compounds can be present in their commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as by a good stability to alkali on limed substrates.

In the following Examples, the following active compounds were used:

Active compound I

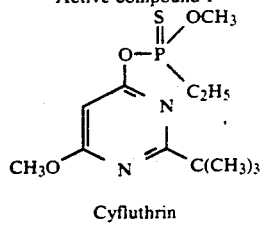

Cyfluthrin

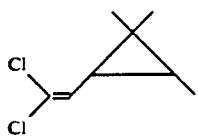

Active compound II

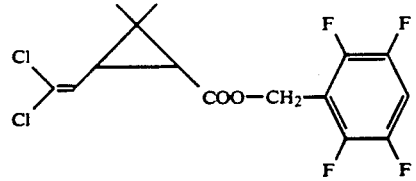

EXAMPLE A

Aerosol tests in 1 m³ chambers

Test method

Three small wire baskets (height 7.8 cm, φ 8 cm) each containing 20 test insects were suspended in the top third of the interior of test chambers made of glass with stainless steel bottoms of the size (internal measurements) $0.84 \times 0.87 \times 1.37$ m = 1 m³ capacity. A defined amount of active compound was dissolved in 2 cm³ of acetone and sprayed by means of pressurized air with the aid of a glass nozzle on the bottom of the chamber.

The time was determined after which 95% of the insects lay motionless on their backs (knock-down time = KT 95). If the KT 95 did not occur within an exposure time of 60 minutes, the percentage of insects which had lasted for the KD was determined. If it was additionally intended to determine the mortality, the insects were transferred to an insecticide-free space in clean cardboard beakers closed with wire gauze and given moisture and sugar, and were tested 24 hours later for % destruction.

| Aerosol action in 1 m³ chambers against resistant *Musca domestica* strain Hans ♂ ♂ |||||
|---|---|---|---|---|
| Active compound ||| 95% knock-down after minutes or % knock-down after one hour ||
| I | mg ai/m³ | II | 95% | 1 hr |
|  |  | 0.5 | 1 hr = 0% | 0 |
| 2.5 |  |  | 1 hr = 0% | 0 |
| 2.5 | + | 0.5 | 1 hr = 71% | 71 |
|  |  | 1 | 1 hr = 13% | 13 |
| 5 |  |  | 1 hr = 25% | 25 |
| 5 | + | 1 | 41' | 100 |
|  |  | 2 | 1 hr = 17% | 17 |
| 10 |  |  | 1 hr = 75% | 75 |
| 10 | + | 2 | 39' | 100 |
|  |  | 0.5 | 1 hr = 0% | 0 |
| 5.0 |  |  | 1 hr = 25% | 25 |
| 5.0 | + | 0.5 | 1 hr = 58% | 58 |
|  |  | 1 | 1 hr = 13% | 13 |
| 10 |  |  | 1 hr = 75% | 75 |
| 10 | + | 1 | 42' | 100 |

| Aerosol action in 1 m³ chambers against resistant *Musca domestica* strain Weymanns ♂ ♂ ||||||
|---|---|---|---|---|---|
| Active compound ||| 95% knock-down after minutes or knock-down after one hour and % mortality after 24 hours |||
| I | mg ai/m³ | II | 95% | 1 hr | 24 hr |
|  |  | 0.1 | 1 hr = 27% | 27 | 0 |
| 0.5 |  |  | 1 hr = 0% | 0 | 2 |
| 0.5 | + | 0.1 | 48' | 67 | 16 |
|  |  | 0.2 | 1 hr = 75% | 75 | 7 |
| 1.0 |  |  | 1 hr = 0% | 0 | 6 |
| 1.0 | + | 0.2 | 39' | 100 | 83 |
|  |  | 0.5 | 1 hr = 92% | 92 | 54 |
| 2.5 |  |  | 1 hr = 0% | 0 | 37 |
| 2.5 | + | 0.5 | 25' | 100 | 100 |
|  |  | 0.1 | 1 hr = 27% | 27 | 0 |
| 1.0 |  |  | 1 hr = 0% | 0 | 6 |
| 1.0 | + | 0.1 | 1 hr = 57% | 57 | 65 |
|  |  | 0.25 | 1 hr = 80% | 80 | 8 |
| 2.5 |  |  | 1 hr = 0% | 0 | 37 |
| 2.5 | + | 0.25 | 34' | 99 | 99 |

EXAMPLE B

Test for residual action

Test method

In order to determine the action of active compounds, various substrates, such as, for example, fired clay and plywood, were sprayed with preparations, formulated as wettable powders (WP), in aqueous suspensions at determined application rates (mg ai/m²).

20 Female house flies of the strain *Musca domestica* were placed on the respective substrates one week after treatment for up to 4 weeks weekly, then additionally after 6 and 8 weeks, etc. The animals were kept on the treated surfaces by means of cages made of wire gauze (height 2 cm, φ 10.7 cm) and remained therein for 24 hours.

The evaluation for percentage destruction was carried out after 15 and 30 minutes, calculated from the time of adding the insects, and also after one to up to 6 hours hourly. Further evaluations were carried out after 8 and 24 hours.

Residual action on various substrates

| Musca domestica strain | Active compound | Formulations | Application rate mg ai/m² | Substrate | Age of the coating in weeks | 100% mortality after hours in the course of an exposure time of 24 hours |
|---|---|---|---|---|---|---|
| Weymanns | cyfluthrin | 10WP | 30 | clay | 3 | 24 hr = 80% |
| " | cyfluthrin | 10WP | 30 | " | 4 | 24 hr = 0% |
| " | I | 40WP | 1000 | clay | 3 | 24 hr = 40% |
| " | I | 40WP | 1000 | " | 4 | 24 hr = 0% |
| " | I + cyfluthrin | 40WP + 10WP | 500 + 30 | clay | 3 | 4 hr |
| " | I + cyfluthrin | 40WP + 10WP | 500 + 30 | " | 4 | 5 hr |
| Kretschmer | cyfluthrin | 10WP | 30 | clay | 1 | 24 hr = 30% |
| " | cyfluthrin | 10WP | 30 | " | 2 | 24 hr = 0% |
| " | I | 40WP | 1000 | clay | 1 | 24 hr = 80% |
| " | I | 40WP | 1000 | " | 2 | 24 hr = 0% |
| " | I + cyfluthrin | 40WP + 10WP | 500 + 30 | clay | 1 | 1 hr |
| " | I + cyfluthrin | 40WP + 10WP | 500 + 30 | " | 2 | 24 hr |
| " | cyfluthrin | 10WP | 30 | wood | 4 | 24 hr = 0% |
| " | I | 40WP | 1000 | " | 4 | 24 hr |
| " | I | 40WP | 1000 | " | 6 | 24 hr |
| " | I | 40WP | 1000 | " | 8 | 24 hr = 80% |
| " | I + cyfluthrin | 40WP + 10WP | 500 + 30 | wood | 4 | 1 hr |
| " | I + cyfluthrin | 40WP + 10WP | 500 + 30 | " | 6 | 2 hr |
| " | I + cyfluthrin | 40WP + 10WP | 500 + 30 | " | 8 | 4 hr |

It is understood that the specification and examples are illustrative but not limitative of the present invention and that other embodiments within the spirit and scope of the invention will suggest themselves to thos skilled in the art.

We claim:

1. An insecticial composition comprising a synergistic insecticidally effective amount of (I) O-(6-methoxy-2-tert.-butyl-pyrimidin-4-yl) O-methyl thionoethanephosphonate of the formula $$\text{(I)}$$

and (II) (4-fluoro-3-phenoxy)-2-cyanobenzyl 2,2-dimethyl-3-(2′,2′-dichlorovinyl)-cyclopropanecarboxylate (cyfluthrin) the synergistic weight ratio of I:II ranging from about 5–50:1.

2. A composition according to claim 1, in which the synergistic weight ratio of I:II is about 5–25:1.

3. A composition according to claim 1, in which the synergistic weight ratio of I:II is about 10–50:1.

4. A method of combating insects which comprises applying to such insects or to an insect habitat a synergistic insecticidal composition according to claim 1.

5. A method of combating insects which comprises applying to such insects or to an insect habitat a synergistic insecticidal composition according to claim 3.